United States Patent
Zadoyan et al.

(10) Patent No.: US 8,057,463 B2
(45) Date of Patent: Nov. 15, 2011

(54) ADAPTIVE PATTERN CORRECTION FOR LASER SCANNERS

(75) Inventors: Ruben Zadoyan, Irvine, CA (US); Michael Karavitis, Seal Beach, CA (US); Peter Goldstein, Santa Ana, CA (US); Mike White, North Tustin, CA (US); Michael Otter, Dana Point, CA (US)

(73) Assignee: AMO Development, LLC., Santa Ana, CA (US)

( * ) Notice: Subject to any disclaimer, the term of this patent is extended or adjusted under 35 U.S.C. 154(b) by 1085 days.

(21) Appl. No.: 11/400,552

(22) Filed: Apr. 7, 2006

(65) Prior Publication Data

US 2007/0235543 A1    Oct. 11, 2007

(51) Int. Cl.
*A61B 18/20* (2006.01)
(52) U.S. Cl. ............ 606/5; 606/4; 235/462.01; 359/326
(58) Field of Classification Search . 606/5; 219/121.66; 359/326
See application file for complete search history.

(56) References Cited

U.S. PATENT DOCUMENTS

| | | | |
|---|---|---|---|
| 3,900,265 A * | 8/1975 | Merlen et al. | 356/431 |
| 4,204,233 A | 5/1980 | Swager | |
| 4,270,131 A * | 5/1981 | Tompkins et al. | 347/250 |
| 4,310,757 A | 1/1982 | Check, Jr. et al. | |
| 4,532,402 A * | 7/1985 | Overbeck | 219/121.78 |
| 4,796,965 A * | 1/1989 | Ishikawa | 359/217.1 |
| 5,469,290 A | 11/1995 | Maeda | |
| 5,638,267 A | 6/1997 | Singhose et al. | 364/148 |
| 5,997,529 A * | 12/1999 | Tang et al. | 606/4 |
| 6,033,396 A * | 3/2000 | Huang et al. | 606/5 |
| 6,706,999 B1 * | 3/2004 | Barrett et al. | 219/121.74 |
| 6,726,325 B2 * | 4/2004 | Xie et al. | 351/209 |
| 7,363,180 B2 * | 4/2008 | Swaringen et al. | 702/85 |
| 2003/0095175 A1 * | 5/2003 | Agorio | 347/247 |
| 2003/0229339 A1 | 12/2003 | Bille | |
| 2004/0254568 A1 * | 12/2004 | Rathjen | 606/4 |
| 2005/0165386 A1 * | 7/2005 | Kurtz et al. | 606/4 |
| 2005/0245915 A1 * | 11/2005 | Loesel et al. | 606/4 |
| 2006/0180581 A1 * | 8/2006 | Swaringen et al. | 219/121.83 |
| 2006/0195076 A1 * | 8/2006 | Blumenkranz et al. | 606/4 |
| 2008/0021443 A1 * | 1/2008 | Bischoff et al. | 606/5 |

OTHER PUBLICATIONS

International Search Report and Written Opinion of PCT Application No. PCT/US07/06458, dated Mar. 6, 2008, 8 pages total.

* cited by examiner

*Primary Examiner* — Henry M Johnson, III
*Assistant Examiner* — Jeffrey Lipitz

(57) ABSTRACT

A system for adaptive laser scanning correction includes a laser scanner coupled to a controller. The controller develops control signals for the laser scanner for a directed scan pattern that is modified to compensate for a characteristic scan-pattern distortion introduced by the laser scanner. The laser scanner responds to the control signals to provide an actual scan pattern approaching a target scan-pattern shape. The system may be useful for ophthalmologic laser surgery and other applications requiring precise control over scan pattern shape and a high scanning speed.

21 Claims, 2 Drawing Sheets

ADAPTIVE PATTERN CORRECTION FOR LASER SCANNERS

BACKGROUND OF THE INVENTION

1. Field of the Invention

The field of the present invention relates laser scanners such as used in laser eye surgery or other applications, and more particularly to procedures for incising the cornea using a laser, and systems for making such incisions, during ophthalmic surgery.

2. Description of Related Art

Laser Assisted In-Situ Keratomileusis (LASIK) and other ophthalmic surgical procedures involve forming a flap of corneal tissue, which is separated from the cornea and folded back to expose underlying stromal tissue. The stromal tissue is then reshaped to correct for conditions such as near-sightedness or astigmatism using a pulsed laser. The laser emits pulses at a known frequency, and each pulse photoalters tissue at the focal point of the laser beam. The focal point of the laser beam is swept over the stromal tissue in a scan pattern, such as a raster pattern, under computer control until the stroma is reshaped as desired. The flap is then folded back over the stroma, to which it becomes reattached during the healing process.

The flap may be cut using a microkeratome, which is a precision surgical instrument with an oscillating blade. In the alternative, the flap may be created using a pattern of laser pulses. To create the corneal flap using a laser, two steps are performed. In one step, a sidecut is created around a desired perimeter of the flap. Both ends of the sidecut terminate without intersecting, thereby leaving an uncut segment that later serves as a hinge for the corneal flap. In another step, the flap is separated from the underlying stromal tissue by scanning the laser focal point over an area called the "resection bed," the perimeter of which is approximately defined by, and slightly larger than, the sidecut. Once the sidecut and the resection bed are made, then the flap can be lifted and folded back to reveal the stromal tissue for reshaping. Suitable surgical equipment for creating the corneal flap using a laser is known in the art.

Laser scanners for ophthalmic surgical systems generally utilize a pair of scanning mirrors or other optics to angularly deflect and scan the laser beam. Scanning mirrors driven by galvanometers may be employed, each scanning the laser along one of two orthogonal axes. A focusing objective, whether one lens or several lenses, images the laser beam onto a focal plane of the optical system. The focal point of the laser beam may thus be scanned in two dimensions (x and y) within the focal plane of the optical system. Scanning along the third dimension, i.e., moving the focal plane along the optical axis (z-axis), may be achieved by moving the focusing objective, or one or more lenses within the focusing objective, along the optical axis. In preparing a corneal bed for flap separation, for example, a circular area may be scanned using a raster pattern driven by the scanning mirrors. The laser photoalters the stromal tissue by scanning the focal point of the laser in a pattern of spots, the distribution of which is determined by the pulse frequency, the scan rate, and the amount of scan line separation.

Generally, higher scan rates, i.e., the step rate at which the focal point of the laser is moved, enable shorter surgical times by increasing the rate at which corneal tissue can be photoaltered. Shorter surgical times are less stressful for the patient, and may reduce the likelihood of errors introduced by excessive movement of the patient. As scan rates increase, greater demands are placed on the laser scanner used to direct the laser beam. Laser scanners used to control the scanning motion may begin to introduce mechanical lag errors in focal point positioning at higher scan rates. It is desirable to correct these errors, without requiring potentially costly changes to laser scanner hardware.

SUMMARY OF THE INVENTION

The present invention provides a method and apparatus for preserving scan pattern fidelity with increasing scan rate. The invention may be applied to adaptively correct scanning errors in response to variable scanning characteristics. The corrections may be accomplished without requiring replacement of existing laser scanner hardware.

In an embodiment of the invention, a laser surgery system is controlled to compensate for positioning errors in scan pattern geometry. The laser scanner comprises optics for a laser beam, and directs the focal point of the laser beam in a scan pattern within a targeted region. The laser scanner may advantageously be controlled by computer. Characteristically, the laser scanner introduces focal point positioning errors in response to scanning movement control signals that result in a distortion of the actual scan pattern. For example, at high scan rates galvanometer lag may prevent the focal point from reaching a theoretical or commanded point, such as the end of an x-axis scan line, before the scan direction is reversed 180°. In such case, the x-axis scan line becomes shorter than intended, and the overall effect is to compress the scan pattern geometry toward a central y-axis. Galvanometer control signals that should result in a circular scan pattern, for example, may result instead in a generally elliptical pattern. The amount of positioning error will be characteristic to a particular laser scanner or type of laser scanner, and may vary with scan rate, spot or scan line separation, or other factors.

Accordingly, the laser scanner is controlled to scan in a directed scan pattern that compensates for the characteristic error. The laser scanner responds to the control signals such that the focal point scans in an actual targeted scan pattern, the targeted scan pattern being different from the directed scan pattern and more closely approximating the desired scan pattern shape. The directed scan pattern causes the actual scan pattern, after introduction of the positioning errors by the laser scanner, to closely approximate the targeted scan pattern. The directed scan pattern may be developed in various different ways, and may encompass any number of separate or related mathematical operations, constants and/or variables that may be applied in developing control signals for the laser scanner. For example, to correct for elliptical error compression in the x-axis, the directed scan pattern may comprise an ellipse with a major axis along the x-axis. Control signals developed to produce the directed scan pattern may thereby cause the actual scan pattern output from the laser scanner, after the introduction of positioning errors, to closely approximate a targeted circular scan pattern.

A suitable directed scan pattern may be used to modify a control output to the laser scanner as a function of one or more independent spatial coordinates, such as 'x' or 'y' coordinates. The directed scan pattern may further be adapted to vary as a function of variables used to control the laser scanner during surgery, such as spot separation and scan rate. Advantageously, the directed scan pattern should be configured to provide the desired scan pattern over a range of different control variable values.

A more complete understanding of the system and method for adaptive pattern correction in laser surgery will be afforded to those skilled in the art, as well as a realization of additional advantages and objects thereof, by a consideration of the following detailed description of the preferred embodiment. Reference will be made to the appended sheets of drawings which will first be described briefly.

DETAILED DESCRIPTION OF THE PREFERRED EMBODIMENT

The present invention provides a system and method for adaptive laser scan pattern correction. The system and method described below may be seamlessly applied in many different areas of technology in which laser scanners are employed. One example of such uses is in the field of laser surgery, and in particular, ophthalmic laser surgery. In the detailed description that follows, adaptive laser scan pattern correction is discussed in the context of ophthalmic laser surgery, and like element numerals are used to denote like elements appearing in one or more of the figures.

In LASIK eye surgery and similar methods, a sidecut is incised in the anterior surface of a cornea using a laser beam during the process of forming a corneal flap. To fully form the corneal flap, the focal point of the laser beam may be directed in a scan pattern to incise corneal tissue underneath the sidecut to form a resection bed. Either of these incisions, or any other surgical laser incision, may be made using an adaptive scan pattern. For example, where a circular resection bed is desired, a directed scan pattern may be employed which defines an elliptical scan pattern. The elliptical scan pattern may be configured such that when output to the laser scanner, and errors in the scan pattern are introduced by the laser scanner, a substantially circular resection bed is created.

Figure 1:
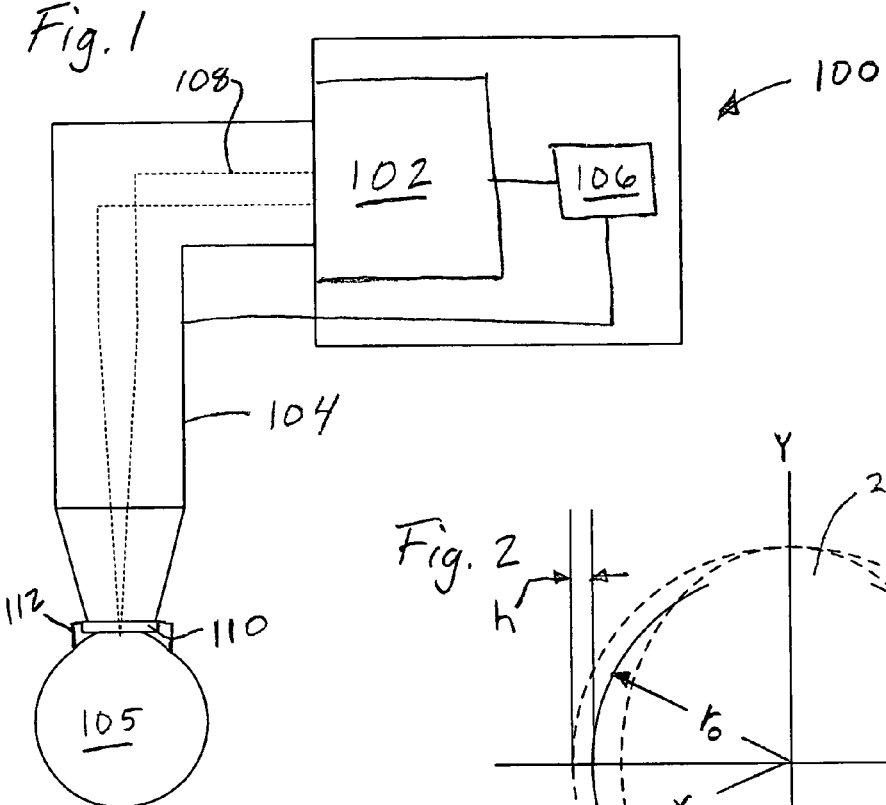
FIG. 1 is a schematic diagram showing an exemplary laser scanning system according to the invention.

Referring to FIG. 1, a laser scanner 100 for ophthalmic laser surgery or other precision scanning application is shown in schematic form. The laser scanner 100 comprises a laser source 102 and optics 104 for directing light from the laser source toward an eye 105 or other target object. Optionally, a laser scanner of the type described in commonly-assigned U.S. patent application Ser. No. 11/258,399, the disclosure of which is incorporated herein by reference, may be employed. A control module 106, such as a computer running suitable control software, may be in communication with optics 104 to direct the focal point of the laser beam 108 in a scan pattern on or in the target object. An applanation lens 110 may be used to flatten the cornea, and may be held in place using a vacuum apparatus 112 as known in the art. The laser source 102 preferably generates a pulsed laser beam. For example, a pulsed laser beam may have a pulse duration as long as a few nanoseconds or as short as a few femtoseconds. One such laser source is described in U.S. Pat. No. 4,764,930, the disclosure of which is incorporated herein by reference. Further details of laser scanners are known in the art, such as described, for example, in U.S. Pat. No. 5,549,632 or U.S. application Ser. No. 11/258,399, the disclosures of which are incorporated herein, in their entirety, by reference.

During ophthalmologic laser surgery, the laser scanner 100 is used to incise a sidecut along a defined periphery on the anterior surface of the cornea, and then to incise a region of stromal tissue generally underneath the sidecut to form a corneal flap. Scanning is accomplished by moving the focal point of the laser beam in increments through a desired scan pattern. The step rate at which the focal point is moved is sometimes called the scan rate; for example, a laser scanner may operate at scan rates between about 10 kHz and 60 kHz, or at any other desired scan rate. For a given scan pattern, the time needed to complete the scan pattern is inversely proportional to the scan rate.

Scanning may be performed in a raster pattern across a region to be scanned. For ophthalmologic applications, the laser focal point may be moved in step increments generally between about 4 μm and 30 μm apart along a raster line, known as a spot separation. Likewise, raster lines are spaced a corresponding distance apart known as a line separation, also usually in the range of about 4 μm to 30 μm apart. Any other useful spot/line separation may be used.

Motion along a raster line is conventionally described as parallel to an 'x' axis of the scanning field, with a perpendicular 'y' axis conventionally defined in the scanning plane. The velocity of the laser beam focal point along the 'x' or "fast" axis will be the product of the scan rate and the spot separation, and is generally much faster than velocity along the 'y' or "slow" axis. Generally, higher velocities are desirable, but at higher scan rates, existing laser scanning equipment may lag noticeably behind commanded laser positions along the fast axis, so as to cause a shortening or compressing of each scan line towards the slow 'y' axis. For example, a circular scan area may become elliptical, with a major axis along the central 'y' axis. The amount of compression is generally characteristic of the type of laser scanner employed, and may vary as a function of spot separation and scan rate. For existing laser scanners, elliptical distortion has been observed at scan rates as low as 15 kHz for large spot separation values. In addition, laser scanners with higher scan rates, such as 30 kHz or 60 kHz, are now available, for which scan pattern distortion may be appreciable regardless of spot separation values. The present invention may be used to eliminate or greatly reduce compressive scanning (e.g., elliptical) distortion in existing scanning equipment without lowering scan velocity.

Figure 2:
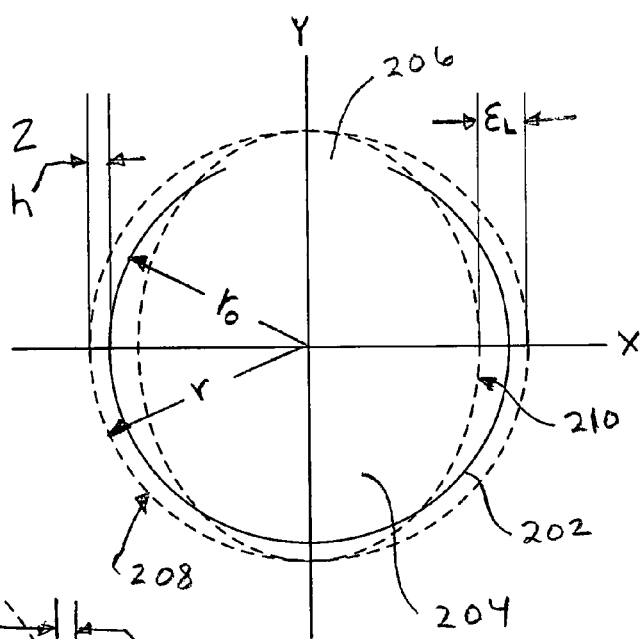
FIG. 2 is a diagram shows an application for scan pattern correction according to the invention.

FIG. 2 is a chart illustrating the foregoing concepts in application to a LASIK or other ophthalmologic laser surgery application. A semi-circular sidecut 202 of radius '$r_o$' may first be cut, conventionally described herein as centered on an 'x' and 'y' axis of a Cartesian coordinate system, although any other coordinate system may also be used. The sidecut 202 is at the periphery of a circular region 204 for forming a flap, under which the resection bed is formed by incising stromal tissue to fully form the flap, which may then be lifted and folded back along a hinge region 206. Accordingly, it is desirable to scan the laser focal point through the stromal tissue over a generally circular resection bed 208 of radius 'r'. In this example, the targeted scan pattern for the laser scanner is therefore circular in shape. The resection bed should be centered on the flap region 204 and provide a substantially uniform horizontal overlap 'h' around and under the sidecut 202, such that $r_o+h=r$. The overlap advantageously ensures that the flap region 204 can be lifted from the stromal tissue without tearing, by providing a margin of safety for positioning or scanning errors. An underlap (i.e., lack of overlap) of more than approximately 20 μm can result in corneal flaps that are difficult to lift, and give rise to undesirable damage to corneal tissue when the flap is lifted. Conversely, extreme overlap (e.g., more than 200 μm) is believed to have little adverse consequences except for a possible reduction in corneal centration range.

FIG. 2 also shows an elliptically distorted resection bed 210, such as may be produced by a laser scanner driven at high velocity when provided with conventional control signals for producing a circular resection bed. The amount of distortion has been exaggerated for illustrative clarity. In this example, a lag in the responsiveness of the laser scanner causes the scan pattern for the resection bed to assume an approximately elliptical shape with the major axis along the 'y' axis. Along the minor 'x' axis, the scanning error causes a maximum discrepancy '$\epsilon_L$' between the target circular bed and the actual elliptical bed created by the laser scanner. This discrepancy reduces or eliminates the horizontal overlap 'h' towards the 'x' axis, and represents an amount of correction that should be introduced in the 'x' direction to ensure continuous overlap of the resection bed and the sidecut 202.

Figure 3:
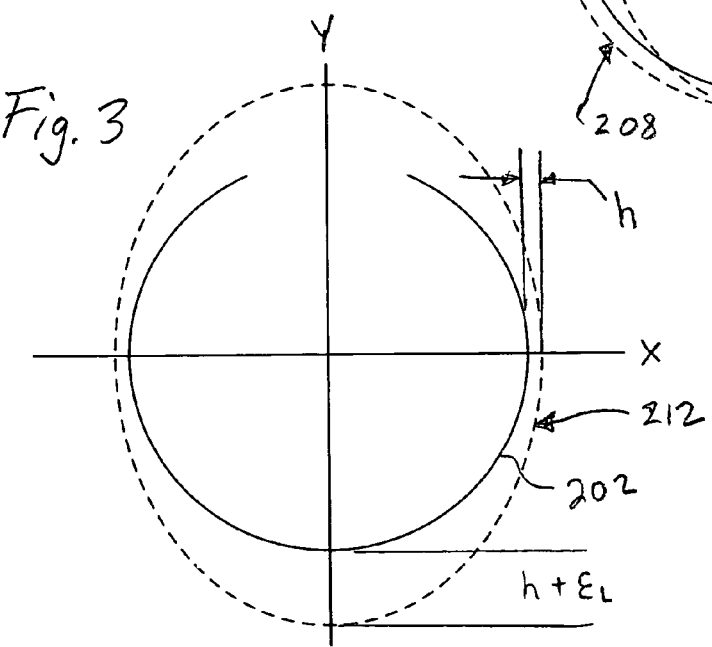
FIG. 3 is a diagram showing a method for compensating for pattern distortion without correcting the distortion.

One approach to ensuring continuous overlap involves simply increasing the radius of the commanded resection bed by an amount equal to $\epsilon_L$. This approach may result in an approximately elliptical resection bed 212 as illustrated in FIG. 3. The resection bed 212 overlaps the sidecut 202 by an amount 'h' along the 'x' axis and by an amount 'h+$\epsilon_L$' along the 'y' axis. This method ensures continuous overlap, but causes excess overlap to occur along the 'y' axis. It may be preferable to minimize or prevent excess overlap using a more sophisticated approach.

To correct scanning error of the type exemplified in FIG. 2, a more sophisticated approach may comprise modifying the commanded scan pattern as a function of at least one spatial variable. For example, the elliptical scanning distortion described above involves error in the 'x' direction, the amount of which varies depending on the 'y' coordinate. To offset this error, a complementary scan pattern may be commanded, in which an amount of error correction in the 'x' direction varies as a function of 'y' position. In particular, an elliptical scan pattern may be commanded, which if not for the scanning error introduced by the laser scanner, would result in an elliptical scan pattern having a major axis along the 'x' axis and a minor axis along the 'y' axis. The major diameter of the directed scan pattern may be 2(r+$\epsilon_L$), wherein 'r' and '$\epsilon_L$' are as defined in connection with FIG. 2. The minor axis may be 2(r+h). Mathematically, such an ellipse may be defined as:

$$\frac{x^2}{(r+\varepsilon_L)^2} + \frac{y^2}{r^2} = A, \quad \text{(Eq. 1)}$$

in which 'x' and 'y' are independent spatial coordinates and 'r' and 'A' are constants selected to obtain the desired radius of the resection bed. Conventionally, 'A' is equal to one, but other values may also be used. While Eq. 1 uses an elliptical relationship to correct for x-axis distortion, other functions, for example, parabolic, polynomial, or linear functions may also be useful.

Figure 4:
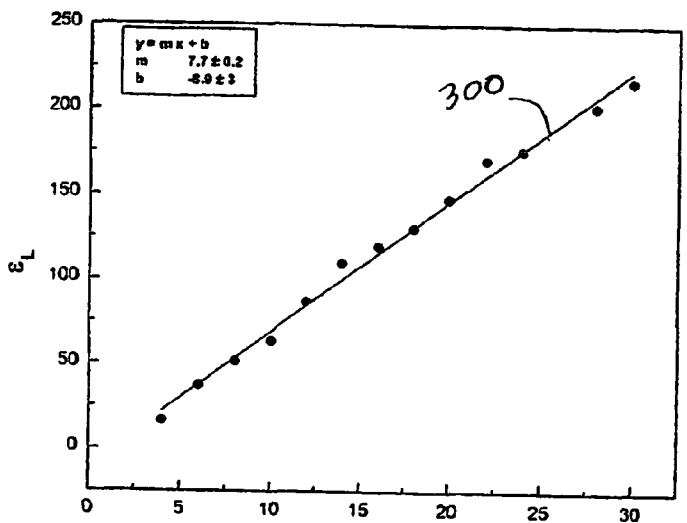
FIG. 4 is a chart showing an exemplary relationship between scan pattern error and laser scanning spot separation.

The correction factor '$\epsilon_L$' may be constant, but in an embodiment of the invention, is determined as a function of other scanning variables. For some laser scanners, the degree of elliptical distortion may vary as a function of scanning velocity, which in turn depends primarily on the scan rate and the spot separation. Therefore, for a fixed scan rate, '$\epsilon_L$' may be shown to be dependent on spot separation. FIG. 4 shows one exemplary relationship 300 between spot separation 'SS', shown on the horizontal axis, and '$\epsilon_L$' shown on the vertical axis, such as may be measured for a laser scanner. Both 'SS' and '$\epsilon_L$' are expressed in microns. Such measurements may be performed by operating on glass slides using different spot separation values, and inspecting the resulting slides microscopically. In this example, a characteristic linear relationship is illustrated, which may be expressed as:

$$\epsilon_L(ss) = B \cdot SS + C, \quad \text{(Eq. 2)}$$

in which 'B' and 'C' are constants determined from the chart shown in FIG. 4. In this example, setting B=7.7 and C=−8.9 results in a good fit with the measured data. Eq. 2 may then be used to determine the value of the correction factor used in Eq. 1, depending on the desired spot separation. Methods of implementing the foregoing corrections in control software for laser scanners should be apparent to one of ordinary skill, and any suitable method may be used.

Figure 6:
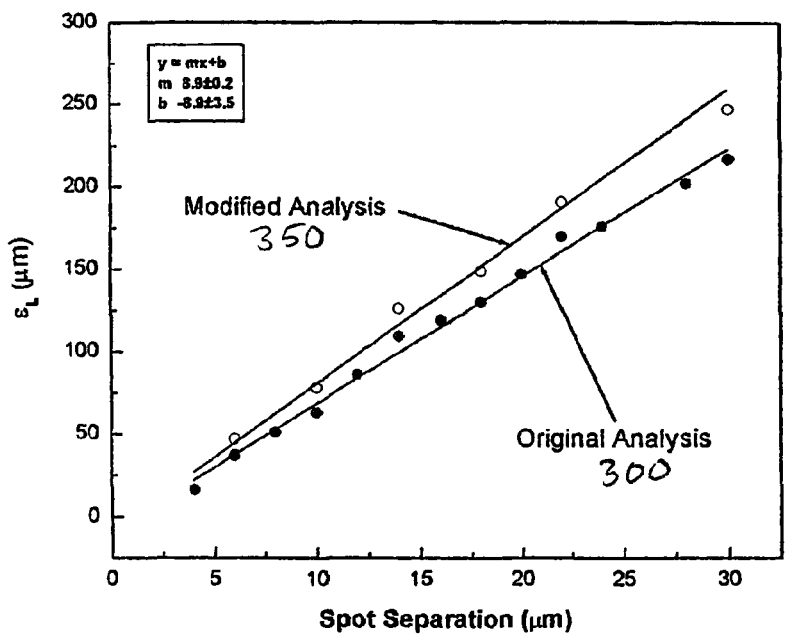
FIG. 6 is a chart showing an exemplary relationship between scan pattern error and laser scanning spot separation, including additional off-axis error.
Figure 5:
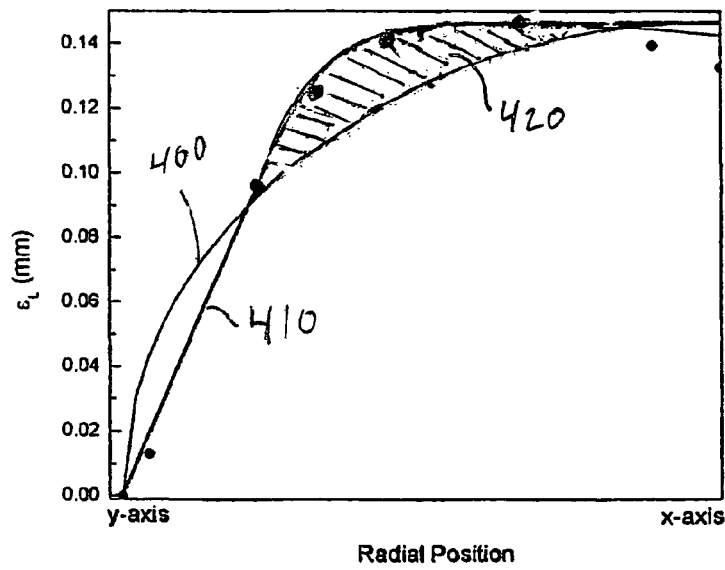
FIG. 5 is a chart showing additional deviation between an exemplary observed scanning error and an elliptical correction.

For some laser scanners, x-axis error may deviate noticeably from an elliptical relationship. FIG. 5 shows an exemplary deviation between an elliptical correction curve 400 and an observed relationship 410 fitted to measurement data. The area 420 between these two curves represents under-corrections in the scan pattern towards the x-axis. This additional deviation may be measured at an appropriate y-axis position, such as at or near (½)r (that is, 45° off the 'x' axis), and charted as a function of spot separation. Exemplary results are shown in FIG. 6. Here, the additional deviation is fitted to a line 350 having a greater slope than the original line 300. In the present example, the increased slope corresponds to a value of B=8.9 in Eq. 2, about 16% greater than previously determined for '$\epsilon_L$' on the 'x' axis. The correction factor '$\epsilon_L$' may be computed using this modified correction factor. It should be apparent that the particular values disclosed herein are by way of example only, and should not be construed as limiting the invention.

For some laser scanners, the amount of elliptical error introduced by the laser scanner may depend on the rise time of the scanner galvanometers in response to a step input, sometime referred to a "galvo tuning." The rise time should typically be in the range of about 1.35 to 1.39 milliseconds, but variation between about 1.2 to 1.8 milliseconds may be possible. It is desirable to provide a laser scanner with a scan pattern adjustment that will prevent both underlap and excessive overlap for these variations in galvo tuning. The example below describes one such solution for an IntraLase™ FS2 30 kHz laser. It should be apparent that different solutions may be developed using the principles disclosed herein for different laser scanners.

Example

An FS2 30 kHz laser was programmed with different radial offset factors for spot separations of 4, 10, 16, 22 and 30 μm, using its factory settings. The laser was configured such that a radial offset of zero generated a theoretically (i.e., ignoring galvanometer lag) circular scan pattern. Entry of a positive radial offset would produce a theoretical elliptical output according to Eq. 1 above. The FS2 laser could also be programmed with an amount of horizontal offset, regardless of spot separation. Factory settings for the FS2 laser were determined and set using the following methodology:
1. Set the horizontal offset to 100 μm.
2. Set the radial offset to zero for all spot separations.
3. Cut 9 mm patterns in glass slides at three spot separations, e.g., 6, 12 and 18 μm.
4. Measure the amount of raster-side (x-axis) overlap at the 0° and 180° positions.

5. Select the set of values for the position (i.e., 0° and 180°) exhibiting the most underlap and least overlap.
6. Perform a linear regression to obtain a slope ('B') and intercept ('C') values for the selected set of values, as a function of spot separation.
7. Add a constant offset (e.g., 30 µm) to the calculated intercept 'C'. The offset should correspond to the targeted amount of overlap.
8. Multiply the slope 'B' by 1.15 to compensate for the non-elliptical shape of the galvanometer lag error in the FS2 laser, as described above.
9. Calculate a radial offset for each spot separation, using Eq. 2 and the values of 'B' and 'C' as derived in steps 7-8 above.
10. Enter the radial offset values into the factory settings for the LS2 laser.

The foregoing method was used to prepare an FS2 laser. The resulting overlap was measured at eight equally-spaced locations around a circular perimeter for spot separations from 6 to 14 µm, using glass slides. Actual measured overlap ranged between 40 and 103 µm over all positions, well within the target range of 30 to 200 µm. The laser galvanometers were then detuned to exhibit rise times of 1.45 to 1.49 milliseconds, and the measurements were repeated. Overlap ranged between 29 and 97 µm, and were generally comfortably within the target overlap range. Next, the galvanometers were detuned to an extreme value of 1.8 milliseconds. Overlap ranged between 0 and 95 µm. While an overlap of 30 µm was not maintained at all positions, a rise time of 1.8 represents an extremely unlikely value for an FS2 laser, and an overlap of zero should still be clinically acceptable. Finally, the galvanometers were retuned to a rise time of 1.25, representing an upper limit on galvanometer performance, and the measurements repeated. All measured overlaps were within the range of 30 to 200 µm and were reasonable for clinical use, i.e., would not limit centration range.

Having thus described a preferred embodiment of a system and method for adaptive pattern correction in laser surgery, it should be apparent to those skilled in the art that certain advantages of the within system have been achieved. It should also be appreciated that various modifications, adaptations, and alternative embodiments thereof may be made within the scope and spirit of the present invention. For example, a method for correcting elliptical error in a scan pattern to achieve a more circular output pattern has been illustrated, but it should be apparent that the inventive concepts described above would be equally applicable to other desired scan pattern shapes. Likewise, the invention is not limited to eye surgery, and may be used with scanning lasers for other applications, including various other surgical or industrial applications where precise control of a scan pattern shape and high scanning rates are desired. The invention is defined by the following claims.

What is claimed is:

1. A method for scanning, with a laser scanner system having a controller and a laser scanner, a focal point of a laser along a desired scan pattern so as to incise an optical tissue of an eye of a patient in an ophthalmic surgical procedure, the method comprising:
receiving, with the controller, an input of the desired scan pattern and a scan rate or spot separation input by a user into the controller;
calculating with the controller a directed scan pattern from the desired scan pattern and the scan rate or spot separation input using an error correction factor, wherein the error correction factor characterizes focal positioning errors, the errors associated with mechanical lag of the laser scanner, wherein the errors are characteristically introduced by the laser scanner and vary with the scan rate or spot separation, and wherein the error correction factor is determined by scanning a plurality of scans of a given scan pattern at differing scan rates or differing spot separations, measuring corresponding focal point positioning errors in each of the plurality of scans of the given scan pattern, and performing a linear regression to determine the error correction factor as a function of the scan rate or spot separation, respectively, wherein the error correction factor '$\epsilon_L$' is determined according to the equation $\epsilon_L(ss)=B\cdot x+C$, wherein 'x' is the spot separation or scan rate, respectively, 'B' is a scalar constant, and 'C' is a scalar constant;
transmitting movement control signals to the laser scanner to scan a focal point of a laser beam along a first axis and along a second axis transverse to the first axis per the directed scan pattern, wherein the control signals are transmitted by the controller to the laser scanner; and
scanning the laser scanner in response to the control signals such that the focal point actually scans in a targeted scan pattern, the targeted scan pattern being different from the directed scan pattern such that the system mitigates distortion of the scan pattern geometry associated with the positioning errors in the first axis before the laser beam is directed to the tissue and wherein the targeted scan pattern more closely approximates the desired scan pattern than does the directed scan pattern.

2. The method of claim 1, wherein calculating with the controller a directed scan pattern further comprises calculating the directed scan pattern as a function of at least one independent spatial coordinate of the directed scan pattern.

3. The method of claim 1, wherein calculating with the controller a directed scan pattern further comprises calculating the directed scan pattern as a function of spot separation.

4. A method for scanning, with a laser scanner system having a controller and a laser scanner, a focal point of a laser along a desired scan pattern so as to incise an optical tissue of an eye of a patient in an ophthalmic surgical procedure, the method comprising:
receiving, with the controller, an input of the desired scan pattern and a scan rate or spot separation input by a user into the controller;
determining the error correction factor '$\epsilon_L$' as a function of spot separation according to the equation $\epsilon_L(ss)=B\cdot SS+C$, wherein 'SS' is the spot separation in the scan pattern, 'B' is a scalar constant, and 'C' is a scalar constant
calculating with the controller a directed scan pattern from the desired scan pattern and the scan rate or spot separation input using an error correction factor, wherein the error correction factor characterizes focal positioning errors, the errors associated with mechanical lag of the laser scanner, wherein the errors are characteristically introduced by the laser scanner and vary with the scan rate or spot separation, and wherein the directed scan pattern comprises an elliptical shape and is defined according to the equation $$\frac{x^2}{(r+\varepsilon_L)^2}+\frac{y^2}{r^2}=A,$$

wherein 'x' is a first axial position coordinate for the first axis, 'y' is a second axial position coordinate for the second axis perpendicular to the first axis, 'r' is a desired radius for the targeted scan pattern, '$\epsilon_L$' is the error correction factor and 'A' is a constant;

transmitting movement control signals to the laser scanner to scan a focal point of a laser beam along a first axis and along a second axis transverse to the first axis per the directed scan pattern, wherein the control signals are transmitted by the controller to the laser scanner; and scanning the laser scanner in response to the control signals such that the focal point actually scans in a targeted scan pattern, wherein the targeted scan pattern comprises a circular shape, the targeted scan pattern being different from the directed scan pattern such that the system mitigates distortion of the scan pattern geometry associated with the positioning errors in the first axis before the laser beam is directed to the tissue and wherein the targeted scan pattern more closely approximates the desired scan pattern than does the directed scan pattern.

5. A system for performing laser scanning, comprising:

a laser scanner configured to direct a laser beam focal point along a first axis and along a second axis transverse to the first axis in a region of tissue, the laser scanner characteristically introducing focal point positioning errors in response to scanning control signals, the positioning errors varying with scan rate or focal point spot separation and associated with mechanical lag of the laser scanner, wherein the positioning errors distort scan pattern geometry; and a controller operatively associated with the laser scanner, the controller configured to calculate a directed scan pattern and transmit control signals to the laser scanner to scan the focal point according to the directed scan pattern, the directed scan pattern determined by the controller using an error correction factor, a desired scan pattern and a scan rate or a spot separation of the laser scanner, wherein the correction factor characterizes the positioning errors of the laser scanner at the desired scan rate or spot separation of the laser scanner and wherein the error correction factor is determined by scanning a plurality of scans of a given scan pattern at differing scan rates or differing spot separations, measuring corresponding focal point positioning errors in each of the plurality of scans of the given scan pattern, and performing a linear regression to determine the error correction factor as a function of the scan rate or spot separation, respectively, wherein the error correction factor '$\epsilon_L$' is determined according to the equation $\epsilon_L(ss)=B\cdot x+C$, wherein 'x' is the spot separation or scan rate, respectively, 'B' is a scalar constant, and 'C' is a scalar constant, wherein the directed scan pattern is adapted, per the correction factor, to compensate for the positioning errors such that the focal point scans in a targeted scan pattern, the targeted scan pattern being different from the directed scan pattern so that the system mitigates distortion of the scan pattern geometry associated with the positioning errors in the first axis before the laser beam is directed to the tissue such that the targeted scan pattern more closely approximates a desired scan pattern than does the directed scan pattern.

6. The system of claim 5, wherein the controller is further configured to calculate the directed scan pattern as a function of at least one independent spatial coordinate of the directed scan pattern.

7. The system of claim 5, wherein the error correction factor is determined as a function of spot separation and wherein the controller is further configured to calculate the directed scan pattern as a function of spot separation using the error correction factor.

8. The system of claim 5, wherein the directed scan pattern comprises an elliptical shape, and the targeted scan pattern comprises a circular shape.

9. The system of claim 8, wherein the directed scan pattern is defined according to the equation $$\frac{x^2}{(r+\varepsilon_L)^2} + \frac{y^2}{r^2} = A,$$

wherein 'x' is a first axial position coordinate for the first axis, 'y' is a second axial position coordinate for the second axis perpendicular to the first axis, 'r' is a desired radius for the targeted scan pattern, '$\epsilon_L$' is the error correction factor and 'A' is a constant.

10. A method for performing ophthalmologic laser surgery with a laser scanner system having a controller and a laser scanner, the method comprising:

transmitting movement control signals from the controller to the laser scanner to incise a sidecut in an anterior surface of a cornea, the sidecut being incised substantially about a defined perimeter;

receiving, with the controller, a desired scan pattern and a scan rate or focal point spot separation;

calculating a directed scan pattern with the controller from the desired scan pattern from the scan rate and/or spot separation of the desired scan pattern, wherein the directed scan pattern is adapted using an error correction factor to compensate for positioning errors characteristically introduced by the laser scanner during scanning that distort scan pattern geometry, the positioning errors varying with the scan rate or spot separation and associated with mechanical lag of the laser scanner, wherein the error correction factor characterizes the positioning errors and is determined by scanning a plurality of scans of a given scan pattern at differing scan rates or differing spot separations, measuring corresponding focal point positioning errors in each of the plurality of scans of the given scan pattern, and performing a linear regression to determine the error correction factor as a function of the scan rate or spot separation, respectively, wherein the error correction factor '$\epsilon_L$' is determined according to the equation $\epsilon_L(ss)=B\cdot x+C$, wherein 'x' is the spot separation or scan rate, respectively, 'B' is a scalar constant, and 'C' is a scalar constant; and transmitting movement control signals to a laser scanner with scanning control signals to scan a focal point of a laser beam along a first axis and along a second axis transverse to the first axis in the directed scan pattern within a stromal tissue region of the cornea so that the focal point scans in a targeted scan pattern such that the targeted scan pattern more closely approximates the desired scan pattern than does the directed scan pattern, the targeted scan pattern being different from the directed scan pattern such that the system mitigates distortion of the scan pattern geometry associated with the positioning errors in the first axis before the laser beam is directed to the tissue, and wherein the stromal tissue region underlies the sidecut.

11. The method of claim 10, wherein calculating with the controller a directed scan pattern further comprises calculating the directed scan pattern as a function of at least one independent spatial coordinate of the directed scan pattern.

12. The method of claim 10, wherein the error correction factor is determined as a function of spot separation and calculating with the controller a directed scan pattern further comprises calculating the directed scan pattern as a function of spot separation using the error correction factor.

13. The method of claim 10, wherein the directed scan pattern comprises an elliptical shape, and the targeted scan pattern comprises a circular shape.

14. The method of claim 13, wherein the directed scan pattern is defined according to the equation $$\frac{x^2}{(r+\varepsilon_L)^2} + \frac{y^2}{r^2} = A$$

wherein 'x' is a first axial position coordinate for the first axis, 'y' is a second axial position coordinate for the second axis perpendicular to the first axis, 'r' is a desired radius for the targeted scan pattern, '$\varepsilon_L$' is the error correction factor and 'A' is a constant.

15. A system for performing ophthalmologic laser surgery, comprising:
    a laser scanner configured to direct a laser beam focal point along a first axis and along a second axis transverse to the first axis in a region of tissue, the laser scanner characteristically introducing focal point positioning errors in response to scanning control signals, the positioning errors varying with scan rate or spot separation and associated with mechanical lag of the laser scanner, wherein the positioning errors distort scan pattern geometry; and
    a controller operatively associated with the laser scanner, the controller configured to:
    incise a sidecut in an anterior surface of a cornea, the sidecut being incised substantially about a defined perimeter;
    calculate a directed scan pattern using an error correction factor, wherein the error correction factor characterizes the errors and is determined by scanning a plurality of scans of a given scan pattern at differing scan rates or differing spot separations, measuring corresponding focal point positioning errors in each of the plurality of scans of the given scan pattern, and performing a linear regression to determine the error correction factor as a function of the scan rate or spot separation, respectively, wherein the error correction factor '$\varepsilon_L$' is determined according to the equation $\varepsilon_L(ss)=B\cdot x+C$, wherein 'x' is the spot separation or scan rate, respectively, 'B' is a scalar constant, and 'C' is a scalar constant; and
    transmit movement control signals to the laser scanner to scan the focal point in the directed scan pattern within a stromal tissue region of the cornea, wherein the directed scan pattern is adapted by the controller to compensate for the positioning errors such that the focal point scans in a targeted scan pattern, the targeted scan pattern being different from the directed scan pattern, and wherein the stroma tissue region underlies the sidecut so that the system mitigates distortion of the scan pattern geometry associated with the positioning errors in the first axis before the laser beam is directed to the tissue such that the targeted scan pattern more closely approximates a desired scan pattern than does the directed scan pattern.

16. The system of claim 15, wherein the controller is further configured to calculate the directed scan pattern as a function of at least one independent spatial coordinate.

17. The system of claim 15, wherein the error correction factor is determined as a function of spot separation and wherein the controller is further configured to calculate the directed scan pattern as a function of spot separation using the error correction factor.

18. The system of claim 15, wherein the directed scan pattern comprises an elliptical shape, and the targeted scan pattern comprises a circular shape.

19. The system of claim 18, wherein the directed scan pattern is defined according to the equation $$\frac{x^2}{(r+\varepsilon_L)^2} + \frac{y^2}{r^2} = A,$$

wherein 'x' is a first axial position coordinate for the first axis, 'y' is a second axial position coordinate for the second axis perpendicular to the first axis, 'r' is a desired radius for the targeted scan pattern, '$\varepsilon_L$' is the error correction factor and 'A' is a constant.

20. A method for scanning, with a laser scanner system having a controller and a laser scanner, a focal point of a laser along a desired scan pattern so as to incise an optical tissue of an eye of a patient in an ophthalmic surgical procedure, the method comprising:
    receiving, with the controller, a user input of the desired scan pattern and a focal point spot separation for scanning with the laser scanner, the desired scan pattern comprising a circular shape, wherein the laser scanner characteristically introduces focal point positioning errors associated with mechanical lag of the laser scanner that distort scan pattern geometry during scanning;
    calculating an error correction factor '$\varepsilon_L$' which characterizes the errors, wherein '$\varepsilon_L$' is determined by scanning a plurality of scans of a given scan pattern at differing scan rates or differing spot separations, measuring corresponding focal point positioning errors in each of the plurality of scans of the given scan pattern, and performing a linear regression to determine the error correction factor as a function of spot separation according to the equation $\varepsilon_L(ss)=B\cdot SS+C$, wherein 'SS' is the spot separation in the scan pattern, 'B' is a scalar constant, and 'C' is a scalar constant;
    calculating a directed scan pattern using the correction factor, the directed scan pattern comprising an elliptical shape according to the equation $$\frac{x^2}{(r+\varepsilon_L)^2} + \frac{y^2}{r^2} = A,$$

wherein 'x' is a first axial position coordinate for a first axis, 'y' is a second axial position coordinate for a second axis perpendicular to the first axis, 'r' is a desired radius for the scan pattern, '$\varepsilon_L$' is the error correction factor and 'A' is a constant;
    transmitting movement control signals to the laser scanner to scan a focal point of a laser beam of the laser scanner along the first axis and along the second axis per the directed scan pattern;
    scanning the laser scanner in response to the control signals such that the focal point actually scans in a targeted scan pattern, the targeted scan pattern comprising a circular shape, such that the directed scan pattern mitigates distortion of the scan pattern geometry associated with the positioning errors in the first axis before the laser beam is directed to the tissue, the targeted scan pattern more closely approximating the desired scan pattern than does the directed scan pattern.

21. The method of claim 20, wherein the laser scanner scans at a scan rate, and further comprising:
    empirically deriving 'B' and 'C' at the scan rate at which the laser scanner scans the targeted scan pattern.

* * * * *